United States Patent [19]

Graham et al.

[11] Patent Number: 6,040,440
[45] Date of Patent: Mar. 21, 2000

[54] HYPOPHOSPHITE DEOXYGENATION REACTIONS IN THE SYNTHESIS OF ERYTHROMYCIN DERIVATIVES

[75] Inventors: Alexandra E. Graham, Mundelein; Albert V. Thomas, Libertyville; Rachel R. P. Yang, Park City, all of Ill.

[73] Assignee: Abbott Laboratories, Abbott Park, Ill.

[21] Appl. No.: 09/036,186

[22] Filed: Mar. 6, 1998

[51] Int. Cl.$^7$ .............................. C07H 17/08; C07H 1/03
[52] U.S. Cl. ............................................ 536/124; 536/7.2
[58] Field of Search ...................................... 536/7.2, 124

[56] References Cited

U.S. PATENT DOCUMENTS 3,478,013  11/1969  Jones et al. .............................. 536/7.3
5,760,198   6/1998  Parekh et al. ............................ 536/7.2

FOREIGN PATENT DOCUMENTS

WO 93/13780  7/1993  WIPO .
  9822488    5/1998  WIPO .

OTHER PUBLICATIONS

Graham et al., "A New Initiator for Radical Deoxygenations: Application to the Synthesis of 4"–Deoxyerythromycins, " published Sep. 7–11, 1997, Las Vegas, NV, 214th American Chemical Society National Meeting, see entire document.

"Phase–Transfer Catalysis," in *Eastman Organic Chemical Bulletin*, 48(1), 1–2. 1976.

Gokel et al., "Phase Transfer Catalysis—Part I: General Principles," *Journal of Chemical Education*, 55(6), 350–354 (Jun., 1978).

Dehmlow, "Phasentransfer–Katalyse. Eine Veilseitige, Moderne Synthesetechnik mit Potentialler Bedeutung für die Farbenchemie," *Chimia*, 34(1), 12–20 (Jan. 1980).

Graham et al., "A New Initiator for Radical Deoxygenations: Application to the Synthesis of 4"–Deoxyerythromycins," Abstract No. 22, ORGN, *Abstract of Papers, Part 2, 214th National Meeting—American Chemical Society*, Las Vegas, NV, Sep. 7–11, 1997.

Shankaran et al., "Preparation and Activities of 4"–Epi and 4"–Deoxy-4"–amino Analogs Derived from 9–Deoxo–8a–aza–8a–homoerythromycin A$^1$," *Bioorganic &Medicinal Chemistry Letters*, 4(9), 1111–1116 (May 5, 1994).

Journal of Organic Chemistry, vol. 58, No. 24 , (1993), pp. 6838–6842, Barton et al., "The Invention of Radical Reactions. 32. Radical Deoxygenations, Dehalogenations, and Deaminations with Dialkyl Phosphites and Hypophosphorous Acid as Hydrogen Sources".

Heterocycles, vol. 42, No. 2 (1996), pp. 499–502, T. Sato et al., "Practical Radical Deoxygenation of Erythromycins by Barton Reaction".

*Primary Examiner*—L. Eric Crane
*Attorney, Agent, or Firm*—Mona Anand; Portia Chen

[57] ABSTRACT

A process for the preparation of 4"-deoxyerythromycins, having the formula:

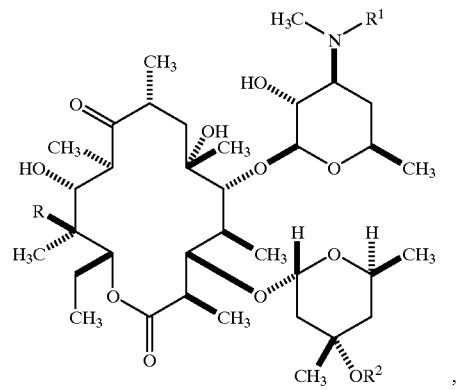

wherein R is H or OH, $R^1$ is H or loweralkyl, and $R^2$ is H or $CH_3$ by treatment of the starting material, 2'-O-acetyl-4"-imidazolylthiocarbamoyl-erythromycin, with a hypophosphite reagent, in a water-miscible protic solvent optionally comprising a phase transfer agent. In a preferred embodiment, the water-miscible solvent is an alcohol and the starting material is reacted with sodium hypophosphite, ACVA and tetra-n-butylammonium hydroxide.

21 Claims, No Drawings

HYPOPHOSPHITE DEOXYGENATION REACTIONS IN THE SYNTHESIS OF ERYTHROMYCIN DERIVATIVES

TECHNICAL FIELD

The present invention relates to a process for the preparation of 4"-deoxyerythromycins A and B, which have use as intermediates in the preparation of gastrointestinal prokinetic agents.

BACKGROUND OF THE INVENTION

Erythromycins (A) through (D), represented by formula (E),

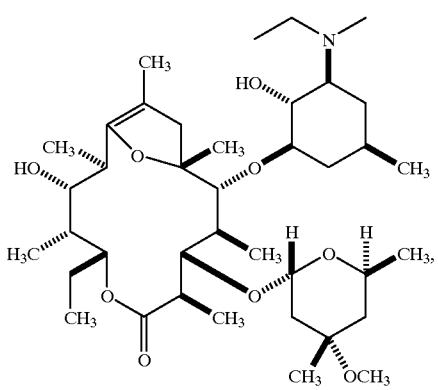

| Erythromycin | $R^a$ | $R^b$ |
|---|---|---|
| (A) | —OH | —$CH_3$ |
| (B) | —H | —$CH_3$ |
| (C) | —OH | —H |
| (D) | —H | —H | are well-known and potent antibacterial agents, used widely to treat and prevent bacterial infections.

A recently developed erythromycin derivative having the formula:

I has been described as a prokinetic agent having use in the treatment of gastrointestinal motility disorders (P. A. Lartey, et al., *J. Med. Chem.*, 38 (1793–1798 (1995); R. Faghih, et al., PCT application WO 9313780, published Jul. 22, 1993). The preparation of the above compound requires the preparation of the intermediate compound, namely, 4"-deoxyerythromycin B.

In the process for the deoxygenation of erythromycins, the 4"-hydroxyl group is initially derivatized as a thiocarbamate. This requires prior protection of the more reactive 2'-hydroxyl group as the acetate. Deoxygenation at the 4"-position of erythromycin with the aid of dialkyl phosphites and hypophosphorous acid has been reported by Barton, S., et al., *J. Org. Chem*, 58:6838–42 (1993).

A process for deoxygenation of the 4"-hydroxy group of the erythromycins A and B by the treatment of starting materials, 2'-O-acetyl-4"-imidazolylthiocarbamoyl-erythromycins A and B using hypophosphorus acid in the presence of a radical initiator 4,4'-azobis-(4-cyanovaleric acid) (ACVA) is described in a commonly-owned co-pending U.S. patent application Ser. No. 08/785,451.

However, there still exists a need for an improved and more efficient method for the synthesis and manufacture of the 4"-deoxygenated erythromycin derivatives to provide cheaper and more widely available desired prokinetic agents.

SUMMARY OF THE INVENTION

Prior attempts at deoxygenation with inorganic hypophosphite salts have been unsuccessful as reported in Barton et al. supra. It has been surprisingly found that deoxygenation of the 4"-hydroxyl group in an erythromycin derivative can be achieved by treatment of the erythromycin derivative with an inorganic salt of hypophosphorus acid in the presence of a free radical initiator in a water-miscible protic solvent at pH 6.5–8.5. The reaction may be carried out with or without the presence of a phase transfer agent. The phase transfer agent is used in those instances wherein the reaction mixture is a two-phase mixture depending on the relative solubilities of the free radical initiator and the hypophosphite salt in the solvent system.

In a first embodiment, the present invention relates to a process for the preparation of 4"-deoxyerythromycins having the formula (II):

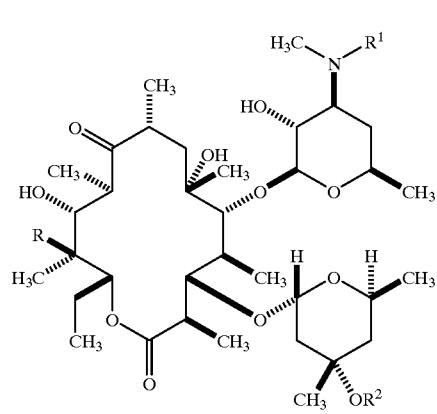

wherein R is H or OH, $R^1$ is H or loweralkyl, and $R^2$ is H or $CH_3$, the process comprises the steps of:

(a) reacting a compound having the formula (III):

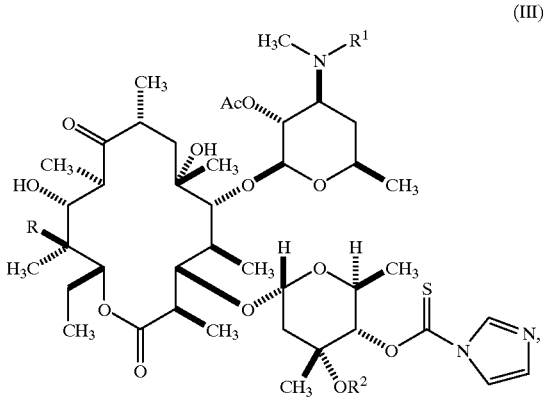

with an inorganic hypophosphite salt and a free radical initiator in a water-miscible protic solvent, to form a compound having the formula (IV):

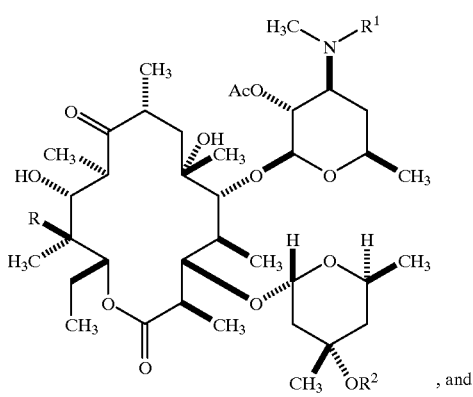

, and (b) removing the 2'-acetyl group.

In a second embodiment, the present invention relates to a process for the preparation of 4"-deoxyerythromycins having the formula (II):

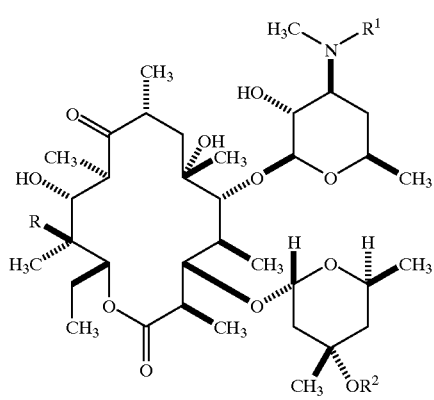

wherein R is H or OH, $R^1$ is H or loweralkyl, and $R^2$ is H or $CH_3$, the process comprises the steps of:

(a) reacting a compound having the formula (III):

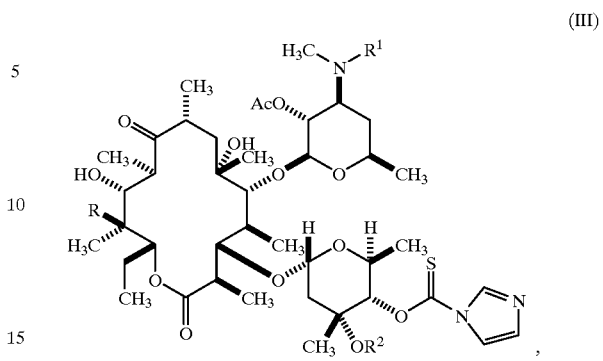

wherein R, $R^1$ and $R^2$ are as defined above; with an inorganic hypophosphite salt, and a free radical initiator in a water-miscible protic solvent, in presence of a phase transfer agent to form a compound having the formula (IV):

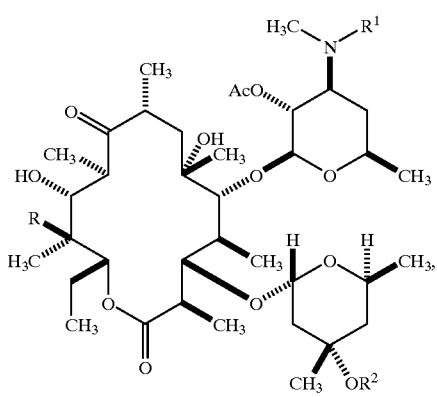

wherein $R^1$ is as defined above; and (b) removing the 2'-acetyl group.

DETAILED DESCRIPTION OF THE INVENTION

Definitions

The following terms are used herein to designate particular elements of the present invention.

The term "loweralkyl" refers to alkyl radicals having from 1 to 6 carbon atoms. Examples of loweralkyl groups include methyl, ethyl, propyl, iso-propyl, butyl, t-butyl, pentyl, hexyl, and the like.

The term "free radical initiator" refers to a compound which is capable of initiating formation of a free radical. For example, an azo initiator catalyzes release of a phosphite radical anion when reacted with a hypophosphite reagent. Examples of suitable free radical initiators include, but are not limited to: 4,4'-azobis-(4-cyanovaleric acid) (ACVA); 2,2'-azobis[2-(imidazolin-2-yl)propane]dihydrochloride (AIBP); 2,2-azobis(amidinopropane)-dihydrochloride (ABAP); azobis(isobutyronitrile) (AIBN); azobis (cyclohexanecarbonitrile) (ACCN); 2,2'-azobis[2-methyl-N-(2-hydroxyethyl)propionamide); and 2,2-azobis (amidinopropane)-dihydrochloride (ABAP); and the like.

The term "phase transfer agent" is a compound that enhances the reaction rate of two or more reagents in two or more phases when the reaction is inhibited by the phase differentiation between the reagents. Among the different classes of phase transfer agents are quaternary ammonium salts, phosphonium salts, crown ethers, and substituted crown ethers as disclosed in Starks, et al., "Phase-Transfer Catalysis," (Chapman & Hall, New York (1994)), which is herein incorporated by reference. Examples of phase transfer agents include, but are not limited to, tetra-n-butylammonium hydroxide, tetraethyl-ammonium hydroxide, benzyl trimethylammonium hydroxide, benzyl triethylammonium hydroxide, tris[2-(2-methoxyethoxy) ethyl amine, tetra-n-butylphosphonium bromide, and tetra-n-butylammonium hydrogen sulfate.

The process of the invention is illustrated in Scheme I below. The starting material 2'-O-acetyl-4"-imidazolylthiocarbamoyl-erythromycin B III, is prepared according to PCT application WO 9313780, the relevant portions of which are incorporated herein by reference.

The process comprises the steps of treating a solution of the starting material III in a water-miscible protic solvent with a hypophosphite reagent in the presence of a radical initiator to obtain the Compound IV. Examples of water miscible, protic solvents include, but are not limited to, ethanol, isopropanol, n-propanol, 2-methoxyethanol, 2-ethoxyethanol, glycerol, acetonitrile and the like, and mixtures thereof.

The hypophosphite reagent provides a radical anion to initiate the deoxygenation reaction. The hypophosphite reagent has the general formula, $M(H_2PO_2)_x$, wherein M is Na, $NH_4$, K, or Ca, and x is 1 or 2. The preferred reagent is sodium hypophosphite.

The hypophosphite salt is treated with a free radical initiator. The free radical initiator facilitates formation of a phosphite radical anion in the reaction. Both water-soluble and organic-soluble initiators can be used in the process of the invention. Preferably, water-soluble initiators are used since more by-products are possible with the use of organic-soluble initiators.

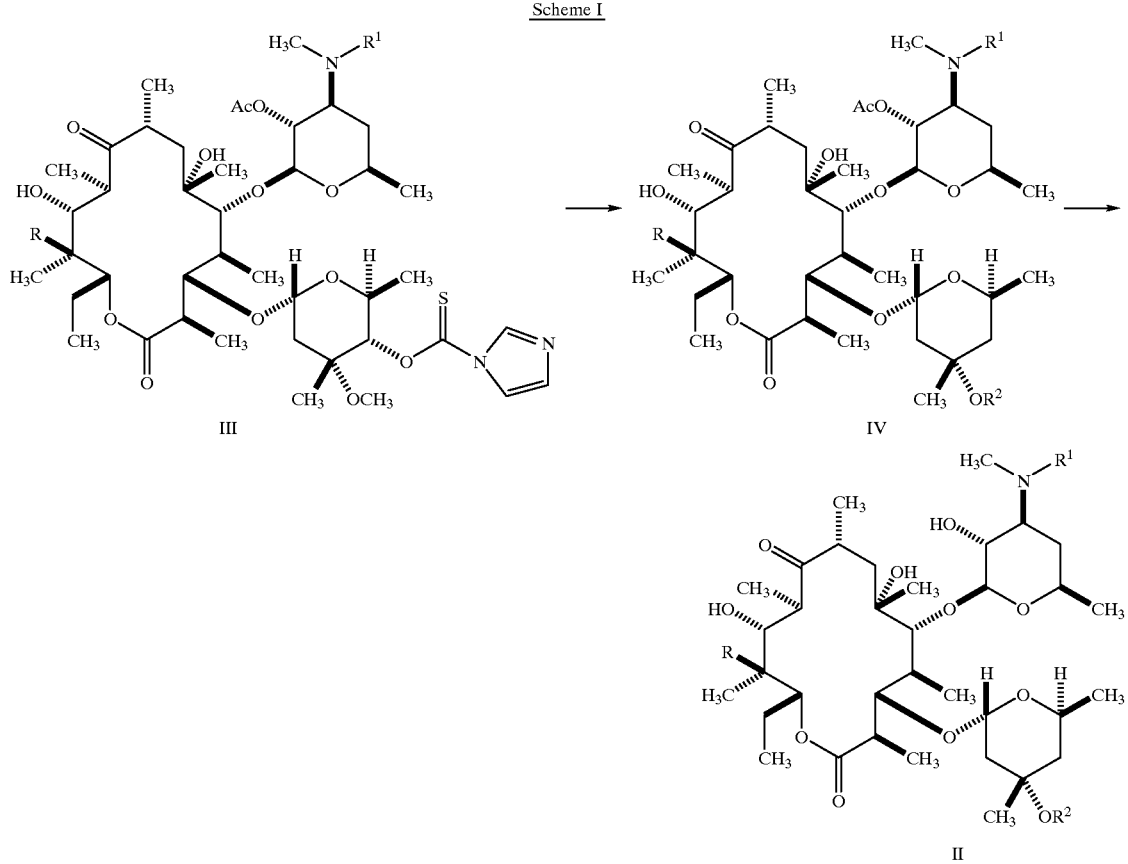

Scheme I

Examples of free radical initiators include, but are not limited to, 4,4'-azobis-(4-cyanovaleric acid) (ACVA); 2,2'-azobis[2-(imidazolin-2-yl)propane]dihydrochloride (AIBP); 2,2-azobis(amidinopropane)-dihydrochloride (ABAP); azobis(isobutyronitrile) (AIBN); azobis (cyclohexanecarbonitrile) (ACCN); 2,2'-azobis[2-methyl-N-(2-hydroxyethyl)-propionamide); and 2,2-azobis (amidinopropane)-dihydrochloride (ABAP). By way of example, an azo initiator, catalyzes release of the phosphite anion radical when reacted with a hypophosphite reagent. Preferably, the free radical initiator is ACVA.

The water solubility of the initiator is of particular advantage, as this property allows the initiator to be separated from the water insoluble 4"-deoxygenated product by partitioning with aqueous base. Preferably, from about 0.1 to 2.0 equivalents of free radical initiator (relative to the starting material) should be added in portions to a solution of starting material in the solvent system.

In the instances, where reaction mixture is a two-phase mixture rather than a one-phase uniform solution of the reactants in the solvent system, the reaction is carried out in the presence of a phase transfer agent.

A phase transfer agent enhances the rate of reaction between the phosphite anion and 2'-O-acetyl-4"-imidazolylthiocarbamoyl-erythromycins A and B (the starting material) and results in an efficient transformation of the starting material to 4"-deoxygenated erythromycins A and B. Among the different classes of phase transfer agents are quaternary ammonium salts, phosphonium salts, crown ethers, and substituted crown ethers as disclosed in Starks, et al., "Phase-Transfer Catalysis," (Chapman & Hall, New York (1994)), which is herein incorporated by reference. Phase transfer agents include, but are not limited to, tris[2-(2-methoxy-ethoxy)ethylamine, tetra-n-butylphosphonium bromide, and tetra-n-butylammonium hydrogen sulfate, tetra-n-butylammonium hydroxide, tetraethylammonium hydroxide, benzyl trimethylammonium hydroxide, benzyl triethylammonium hydroxide, and the like. Preferably, 1-2 equivalents of phase transfer agent are reacted with one equivalent of starting material.

Table 1 below illustrates, for example, the relative solubilities of sodium hypophosphite and the initiator in different solvent systems and the need for using a phase transfer agent in the reaction medium.

TABLE 1

| Solvents | Solubility of NaH2PO2 in solvent | Initiator | Initiator Soluble | Phase Transfer Needed |
| --- | --- | --- | --- | --- |
| Type 1: Ethanol, iso-propanol, 1- propanol or mixtures thereof. | Partially | ACVA AIBN | Yes | Yes |
| Type 1: Ethanol, iso-propanol, 1- propanol or mixtures thereof. | Partially | ACCN AMHP | No | Yes |
| Type 2: 2-Methoxyethanol, 2-ethoxyethanol, glycerol etc. or mixtures of Type 2 and Type 1. | Very | ACVA AIBN | Yes | No |
| Type 2: 2-Methoxyethanol, 2-ethoxyethanol, glycerol etc. or mixtures of Type 2 and Type 1. | Very | ACCN AMHP | No | Yes |

The reaction is typically carried out under almost neutral conditions with the pH of the reaction mixture varying from about 6.5 to about 8.5. In certain instances, it may be necessary to use a buffer to adjust the pH within the desired range.

The phase transfer agent used may be a neutral salt such as tetra-n-butylphosphonium bromide, an amine such as Tris[2-(2-methoxyethoxy)ethylamine or a hydroxide such as tetra-n-butylammonium hydroxide. The addition of a buffer is optional in all cases.

The phase transfer agent may be dissolved in a water soluble base. Any water soluble, non-nucleophilic base is suitable for the reaction. Examples of organic bases include, but are not limited to, triethylamine, diisopropylamine, tetramethylguanidine, N-ethylpiperidine, N-methylpiperidine and the like, or a mixture thereof.

Table 2 below illustrates different combinations of phase transfer agents and initiators and the optional use of a base and a buffer in the individual case.

TABLE 2

| Phase Transfer Agent | Initiator | Additional base | Buffer |
| --- | --- | --- | --- |
| Type 1: Hydroxide e.g. Tetra-n-butyl ammonium hydroxide, benzyltrimethylammonium hydroxide etc. | ACVA | No | Optional |
| Type 2: Amine e.g. Tris[2-(2-methoxyethoxy)ethylamine | ACVA | No | Optional |
| Type 3: Salt e.g. tetra-n-butylphosphonium bromide, Tetra-n-butyl ammonium hydrogensulfate etc. | ACVA | Yes | Optional |
| Types 1–2 | AIBN ACCN AMHP | No | Yes |
| Type 3 | AIBN ACCN AMHP | Optional | Optional |

In a preferred embodiment, the 2'-O-acetyl-4"-imidazolylthiocarbamoyl-erythromycin A or B is treated with sodium hypophosphite in an alcoholic solution and the ACVA radical initiator in the presence of a tetra-n-butylammonium hydroxide phase transfer agent to effect the 4"-deoxygenation. In the preferred embodiment, tetra-n-butylammonium hydroxide acts as both a base and a phase transfer agent.

The reaction is typically carried out at reflux temperature, i.e., between about 75° C. to about 110° C. Preferably, the reaction is carried out at a temperature of from about 90° C. to about 110° C.

Compound IV is deacetylated to obtain the 2'-hydroxy, 4"-deoxy erythromycin derivatives II. The 2'-O-acetate in Compound IV is deprotected using standard procedures well known in the art to yield a 2'-hydroxy, 4"-deoxyerythromycin derivative. By way of example, the 2'-O-acetate Compound IV is treated with methanol in the presence or absence of a weak base and either by application of heat or at room temperature. Ethanol and 1-propanol are also suitable solvents for the deacetylation reaction.

In one embodiment of the process of the invention, R in the starting compound is H.

In another embodiment of the process of the invention, R in the starting compound is OH.

Detailed descriptions of 4"-deoxygenation reactions using processes of the present invention are set forth hereinafter in the Examples. The following Examples illustrate preferred embodiments of the present invention and are not limiting of the specification and claims in any way. The starting materials of Examples 1–18 below, 2'-O-acetyl-4"-imidazolylthiocarbamoyl-erythromycin imidazolylthiocarbamoyl-erythromycin B, was prepared according to PCT application WO 9313780, the relevant portions of which are incorporated herein by reference. The erythromycin A analog, used in Example 8 was prepared by substituting erythromycin A for erythromycin B is the referenced procedure.

EXAMPLE 1

The 2'-O-acetyl-4"-imidazolylthiocarbamoyl erythromycin B (5 g, 5.75 mmol) was dissolved in iso-propanol (50 mL). Sodium hypophosphite (6.1 g, 57.5 mmol), 4,4'-azobis (4-cyanovaleric acid) (1.61 g, 5.75 mmol) and tetra-n-butylammonium hydroxide solution (7 mL of a 1 M solution, 6.9 mmol) were added, under nitrogen to the 2'-O-acetyl-4"-imidazolylthiocarbamoyl erythromycin B.

The mixture was heated to reflux and another portion of tetra-n-butylammonium hydroxide solution was added (3 mL of 1 M solution in methanol, 2.9 mmol). The reaction mixture was heated at reflux for 2 hours and monitored by HPLC for disappearance of starting material. The mixture was cooled to 25 C. and the pH adjusted to 8–8.5 with 10% aqueous sodium bicarbonate. Iso-propanol was removed in vacuo and ethyl acetate (50 mL) and water (50 mL) were added to the residue. The ethyl acetate layer was separated and washed with water (50 mL). Ethyl acetate was removed in vacuo and methanol (25 mL) added to the residue. The solution was heated at 50 C. for 8 hours and the solvent removed to yield crude 4"-deoxyerythromycin B (92.4% yield based on HPLC purity).

EXAMPLE 2

A mixture of iso-propanol (306 mL), sodium hypophosphite (73.82 g, 0.696 mol), 4,4'-azobis(4-cyanovaleric acid) (19.52 g. 0.0696 mol) and tetra-n-butylammonium hydroxide (111.4 mL of a 1 M solution in methanol, 0.111 mol) was heated to reflux, under nitrogen. A solution of 2'-O-acetyl-4"-imidazolylthiocarbamoyl erythromycin B (60.6 g, 0.0696 mol) in iso-propanol (300 mL) was added to the refluxing mixture and the temperature of the mixture maintained above 75 C. The reaction mixture was heated at reflux for 3 hours, monitored by HPLC for disappearance of starting material, and cooled to 25 C. The pH was adjusted to 8.0–8.5 with 10% aqueous sodium bicarbonate. Iso-propanol was removed in vacuo. Ethyl acetate (600 mL) and water (600 mL) were added to the residue. The ethyl acetate layer was separated and washed with water (600 mL). Ethyl acetate was removed in vacuo and methanol (300 mL) added to the residue. The solution was heated at 50 C. for 10 hours and the solvent removed to yield crude 4"-deoxyerythromycin B (84.2% yield based on HPLC purity).

EXAMPLE 3

A mixture of sodium hypophosphite (36.9 g, 0.348 mol) and 2'-O-acetyl-4"-imidazolylthiocarbamoyl erythromycin B (60.6 g, 0.0696 mol) in 1-propanol (606 mL) was heated to reflux. A mixture of 4,4'-azobis(4-cyanovaleric acid) (13.66 g, 0.0488 mol) and tetra-n-butylammonium hydroxide (82.9 mL of 1 M solution in methanol, 0.083 mol) was added in 10 mL portions over 1 hour. The reaction mixture was monitored by HPLC for disappearance of product, then cooled to 45 C. and the pH adjusted to 8.0–8.5 with 10% aqueous sodium bicarbonate. Iso-propanol was removed in vacuo. Ethyl acetate (600 mL) and water (600 mL) were added to the residue. The ethyl acetate layer was separated and washed with water (600 mL). Ethyl acetate was removed in vacuo and methanol (300 mL) was added to the residue. The solution was heated at 50 C. for 8 hours and the solvent was removed to yield crude 4"-deoxyerythromycin B (88.1% yield based on HPLC purity).

EXAMPLE 4

4,4'-Azobis(4-cyanovaleric acid) (8.3 g, 0.0296 mol) was dissolved in a 15 C. solution of tetra-n-butylammonium hydroxide in methanol (45 mL of a 1 M solution, 0.045 mol). One half of the solution was added under nitrogen to a refluxing mixture of sodium hypophosphite (25.12 g, 0.237 mol) in 1-propanol (240 mL) and the mixture was heated to reflux. A mixture of 2'-O-acetyl-4"-imidazolylthiocarbamoyl erythromycin B (34.35 g, 0.0395 mol) in 1-propanol (104 mL) was heated to 45 C. and added to the refluxing mixture. The second half of the solution was added portion wise to the reaction mixture over a period of one hour and the reaction was monitored by HPLC for the disappearance of the starting material. The reaction mixture was cooled to 45 C., the pH adjusted to 8.0–8.5 by addition of 10% aqueous sodium bicarbonate and the solvents removed in vacuo. The residue was partitioned with ethyl acetate (350 mL) and water (350 mL). The ethyl acetate layer was separated and washed with water (350 mL). Ethyl acetate was removed in vacuo. The residue was redissolved in methanol (170 mL). The solution was heated to 50 C. for 10 hours and the methanol was removed to yield crude 4"-deoxyerythromycin B (88.8% yield based on HPLC purity).

EXAMPLE 5

A mixture of ethanol (25 mL), sodium hypophosphite (6.1 g, 57.5 mmol), 4,4'-azobis(4-cyanovaleric acid) (1.61 g, 5.75 mmol) and tetra-n-butylammonium hydroxide (9.2 mL of a 1 M solution in methanol, 9.2 mmol) was heated to reflux, under nitrogen. A warm (45 C.) solution of 2'-O-acetyl-4"-imidazolylthiocarbamoyl erythromycin B (5 g, 5.75 mmol) in ethanol (25 mL) was added to the refluxing mixture. The reaction mixture was heated at reflux for 2 hours, monitored by HPLC for disappearance of starting material, cooled to 45 C., and the pH adjusted to 8.0–8.5 with 10% aqueous sodium bicarbonate. Solvents were removed in vacuo. Ethyl acetate (50 mL) and water (50 mL) were added to the residue. The ethyl acetate layer was separated and washed with water (50 mL). Ethyl acetate was removed in vacuo and methanol (25 mL) added to the residue. The solution was heated at 50 C. for 8 hours and methanol removed to yield crude 4'-deoxyerythromycin B (70.7% yield based on HPLC purity).

EXAMPLE 6

The product was prepared according to the method of Example 5, with the exception that 1-propanol (50 mL), sodium hypophosphite (12.182 g, 114.9 mmol), 4,4'-azobis (4-cyanovaleric acid) (3.22 g, 11.5 mmol), tetra-n-butylammonium hydroxide (20.1 mL of a 1 M solution in methanol, 20.1 mmol) and a solution of 2'-O-acetyl-4"-imidazolylthiocarbamoyl erythromycin B (5 g, 5.75 mmol, in 50 mL of 1-propanol) was used. The reaction mixture was heated at reflux for 1 hour to yield the crude 4"-deoxyerythromycin B (78.6% yield based on HPLC purity).

EXAMPLE 7

The product was prepared according to the method of Example 4, with the exception that 4,4'-azobis(4-cyanovaleric acid) (147.5 g, 0.526 mol), tetra-n-butylammonium hydroxide in methanol (842.1 mL of a 1 M solution, 0.842 mol), sodium hypophosphite (418.4 g, 3.948 mol) in 1-propanol (4 L) and a mixture of 2'-O-acetyl-4,4"-imidazolylthiocarbamoyl erythromycin B (572.5 g, 0.6579 mol), in 1-propanol (1.2 L) were used. The reaction mixture was heated at reflux for 1.25 hours to yield 4"-deoxyerythromycin B which was crystallized from a solution of methanol and water (83.4% isolated yield).

EXAMPLE 8

Sodium hypophosphite (6.1 g, 57.5 mmol) and tetra-n-butylphosphonium bromide (1.95 g, 5.75 mmol) were suspended in 2-methoxyethanol (50 mL) and the pH adjusted to between 7 and 8 with triethylamine. The mixture was heated to 95–100° C., under nitrogen. A portion (½) of the initiator (prepared by dissolving or suspending the desired initiator (5.75 mmol) in 2-methoxyethanol or methanol (15 mL) and adjusting the pH, if necessary, to between 7 and 8) was added to the hot mixture followed by addition of a warm (45 C.) solution of 2'-O-Acetyl-4"-imidazolylthiocarbamoyl erythromycin B ( 5 g, 5.75 mmol) in 2-methoxyethanol (15 mL). The remainder of the initiator was added portion wise to the reaction mixture over 1 hr. and the reaction monitored by HPLC for disappearance of product. The reaction mixture was cooled to 45 C., the pH adjusted to 8–8.5 by addition of 10% aqueous sodium bicarbonate and solvents removed in vacuo. The residue was partitioned with ethyl acetate (50 mL) and water (50 mL), the ethyl acetate layer separated and further washed with water (50 mL). Ethyl acetate was removed in vacuo to afford a residue which was redissolved in methanol (25 mL). The solution was heated at 50 C. for 8–10 hr. and methanol removed to yield crude 4"-deoxyerythromycin B. (% yield based on HPLC analysis given in Table 3).

TABLE 3

| Example | Initiator | Reaction completion (from HPLC) | HPLC Yield |
| --- | --- | --- | --- |
| 8 | ACCN | 1 hr. | 71.5 |
| 9 | AIBN | 20 min. | 75.3 |
| 10 | ACVA | 20 min. | 95.0 |
| 11 | AMHP | 1 hr. | 86.1 |

EXAMPLES 12–14

4,4'-Azobis(4-cyanovaleric acid) (1.13 g, 4 mmol) was suspended in cold propanol (10 mL) and the pH adjusted to between 7 and 8 with cold PTC solution. A portion (⅔) of the above solution (Mixture A) was added, under nitrogen, to a refluxing mixture of sodium hypophosphite (3.05 g, 28.75 mmol) in 1-propanol (50 mL). A warm (45 C.) solution of 2'-O-Acetyl-4"-imidazolylthiocarbamoyl erythromycin B (5 g, 5.75 mmol) in 1-propanol (15 mL) was added to the refluxing mixture. The remainder of mixture A was added portion wise to the reaction mixture over 1 hr. and the reaction monitored by HPLC for disappearance of product. The reaction mixture was cooled to 45 C., the pH adjusted to 8– 8.5 by addition of 10% aqueous sodium bicarbonate and solvents removed in vacuo. The residue was partitioned with ethyl acetate (50 mL) and water (50 mL), the ethyl acetate layer was separated and further washed with water (50 mL). Ethyl acetate was removed in vacuo to afford a residue which was redissolved in methanol (25 mL). The solution was heated at 50 C. for 8–10 hr. and methanol removed to yield crude 4"-deoxy-erythromycin B. The % yield, based on HPLC analysis, are given in Table 4.

TABLE 4

| Example | Phase Transfer Agent (PTA) | mmoles (PTA) | HPLC Yield |
| --- | --- | --- | --- |
| 12 | Tetra-n-butylammonium hydroxide (40% solution in methanol) | 5.75 | 89.3 |
| 13 | Benzyl triethylammonium hydroxide (40% solution in methanol) | 6.14 | 90.7 |
| 14 | Tris[2-(2-methoxyethoxy) ethylamine (TDA) | 5.75 | 87.8 |

EXAMPLE 15

4"-Deoxyerythromycin A

The product was prepared according to the method of Example 4, with the exception that 4,4'-Azobis(4-cyanovaleric acid) (1.19 g, 4.23 mmol), tetra-n-butylammonium hydroxide in methanol (7.16 mL of a 1 M solution, 7.16 mmol), sodium hypophosphite (3.59 g, 33.8 mmol) in 1-propanol (40 mL) and a mixture of 2'-O-Acetyl-4"-imidazolylthiocarbamoyl erythromycin B (5 g, 5.64 mmol, in 1-propanol) were employed. The reaction mixture was heated at reflux for 50 min. This example afforded crude 4"-deoxyerythromycin A, 4.1 g.

EXAMPLES 16 AND 17

Preparation of 4"-Deoxyerythromycin B without the use of the phase transfer agent Examples 16 and 17 illustrate the process of the invention without the need for a phase transfer agent by carrying out the reaction in 2-methoxyethanol using AIBN and ACVA as initiators. Both AIBN and ACVA are soluble in 2-methoxyethanol thereby eliminating the need for the phase transfer agent.

EXAMPLE 16

4,4'-Azobis(4-cyanovaleric acid) (1.61 g, 5.75 mmol) was dissolved in cold 2-methoxyethanol (10 mL) and the pH adjusted to between 7 and 8 with triethylamine. A portion (⅔) of the above solution (Mixture A) was added, under nitrogen, to a refluxing mixture of sodium hypophosphite (3.05 g, 28.75 mmol) in 1-propanol (50 mL). A warm (45 C.) solution of 2'-O-Acetyl-4"-imidazolylthiocarbamoyl erythromycin B (5 g, 5.75 mmol) in 15 mL 1-propanol was added to the refluxing mixture. The remainder of mixture A was added portion wise to the reaction mixture over 40 minutes and the reaction monitored by HPLC for disappearance of product. The reaction mixture was cooled to 45 C., the pH adjusted to 8–8.5 by addition of 10% aqueous sodium bicarbonate and solvents removed in vacuo. The residue was partitioned with ethyl acetate (50 mL) and water (50 mL), the ethyl acetate layer was separated and further washed with water (50 mL). Ethyl acetate was removed in vacuo to afford a residue which was redissolved in methanol (25 mL). The solution was heated at 50 C. for 8–10 hr. and methanol removed to yield crude 4"-deoxyerythromycin B. (83.6% yield based on HPLC analysis).

EXAMPLE 17

The product was prepared according to the method of Example 4, with the exception that Azobis isobutyronitrile (0.45 g, 3 mmol), sodium hypophosphite (6.1 g, 57.5 mmol) in 1-propanol (50 mL) and a mixture of 2'-O-Acetyl-4"-imidazolylthiocarbamoyl erythromycin B (5 g, 5.75 mmol, in 15 mL 1-propanol) were employed. The reaction mixture was heated at reflux for 20 min. This example afforded crude 4"-deoxyerythromycin B (77.2% based on HPLC analysis).

EXAMPLE 18

Optional addition of buffer (tetramethylguanidine-phosphoric acid buffer) to the reaction mixture to maintain pH in appropriate range)

The pH of a solution of tetramethylguanidine (0.72 mL, 5.75 mmol) in 1-propanol (35 mL) was adjusted to pH 8 with 10% phosphoric acid in 1-propanol. To the resulting slurry was added sodium hypophosphite (6.1 g, 57.5 mmol. The mixture was heated to reflux and a solution of 2'-O-Acetyl-4"-imidazolylthiocarbamoyl erythromycin B (5 g, 5.75 mmol, in 10 mL 1-propanol) was added. 4,4'-Azobis(4-cyanovaleric acid) (0.805 g, 2.875 mmol) was dissolved in cold 2-methoxyethanol (10 mL) and the pH adjusted to between 7 and 8 with triethylamine. This solution was added, under nitrogen, to the refluxing mixture of sodium hypophosphite, buffer and starting material. The reaction mixture was heated at reflux for 20 minutes and monitored by HPLC for disappearance of product. The mixture was cooled to 45 C., the pH adjusted to 8–8.5 by addition of 10% aqueous sodium bicarbonate and solvents removed in vacuo. The residue was partitioned with ethyl acetate (50 mL) and water (50 mL), the ethyl acetate layer separated and further washed with water (50 mL). Ethyl acetate was removed in vacuo to afford a residue which was redissolved in methanol (25 mL). The solution was heated at 50 C. for 8 hr. and methanol removed to yield crude 4"-deoxyerythromycin B.

What is claimed is:

1. A process for preparing a compound having the formula (II):

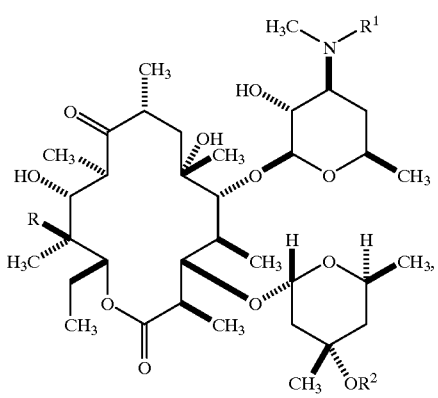

wherein R is H or OH, $R^1$ is H or loweralkyl, and $R^2$ is H or $CH_3$; comprising the steps of:

(a) reacting a starting material compound having the formula (III):

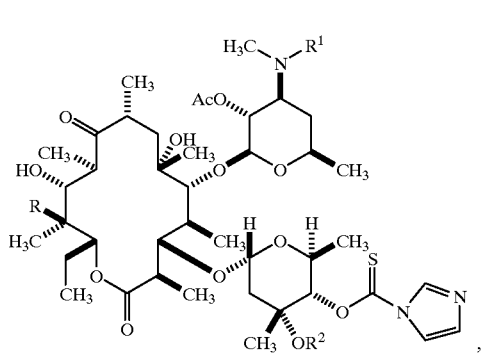

wherein R, $R^1$, and $R^2$ are as defined above;

with an inorganic hypophosphite salt and a free radical initiator in a water-miscible protic solvent, to form a compound having the formula (IV):

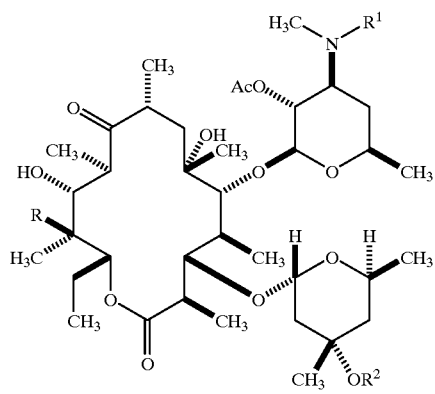

, and (b) removing the 2'-acetyl group.

2. The process according to claim 1, wherein the hypophosphite reagent is a compound having a formula $M(H_2PO_2)_x$, wherein M is $Na^+$, $NH_4^+$, $K^+$, or $Ca^{++}$, and x is 1 or 2.

3. The process according to claim 1, wherein the free radical initiator is selected from the group consisting of 4,4'-azobis-(4-cyanovaleric acid) (ACVA), 2,2'-azobis[2-(imidazolin-2-yl)propane]dihydrochloride (AIBP), 2,2-azobis(amidinopropane)-dihydrochloride (ABAP), azobis (isobutyronitrile) (AIBN), azobis(cyclohexanecarbonitrile) (ACCN), and 2,2'-azobis[2-methyl-N-(2-hydroxyethyl) propionamide) (AMHP).

4. The process according to claim 1, wherein R is H.

5. The process according to claim 1, wherein R is OH.

6. The process according to claim 1 further comprising a phase transfer agent.

7. The process according to claim 6, wherein, the phase transfer agent is selected from the group consisting of tetra-n-butylammonium hydroxide, tetraethylammonium hydroxide, benzyl trimethylammonium hydroxide, benzyl triethylammonium hydroxide, tris[2-(2-methoxyethoxy) ethylamine, tetra-n-butylphosphonium bromide, and tetra-n-butylammonium hydrogen sulfate.

8. The process according to claim 7, wherein the phase transfer agent is dissolved in a solution with a water soluble base.

9. The process according to claim 8, wherein the base is triethylamine, diisopropylamine, tetramethylguanidine, N-ethylpiperidine, N-methylpiperidine, and tetra-n-butylammonium hydroxide or a mixture thereof.

10. The process according to claim 1, wherein the water-miscible solvent is solvent is selected from the group consisting of methanol, ethanol, iso-propanol, n-propanol, and 2-methoxyethanol, or a mixture thereof.

11. The process according to claim 1, wherein the water-miscible solvent is an alcohol wherein the compound is reacted with sodium hypophosphite, ACVA and tetra-n-butylammonium hydroxide.

12. A process for preparing a compound having the formula (II):

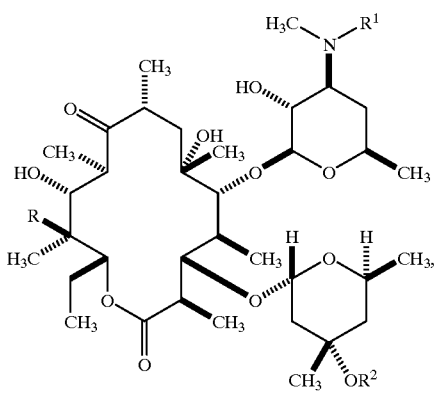
(II)

wherein R is H or OH, R¹ is H or loweralkyl, and R² is H or CH₃; comprising the steps of:

(a) reacting a starting material compound having the formula (III):

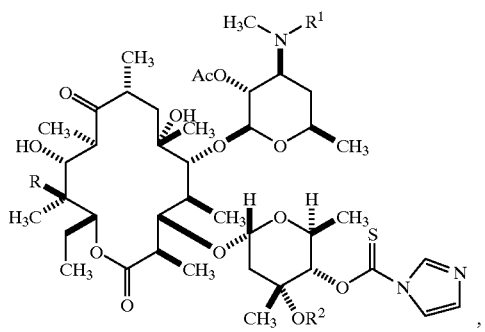
(III)

wherein R, R¹ and R² are as defined above;

with an inorganic hypophosphite salt, and a free radical initiator in a water-miscible protic solvent, in presence of a phase transfer agent to form a compound having the formula (IV):

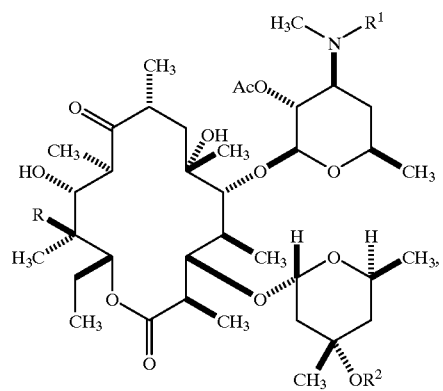
(IV)

wherein R, R¹ and R² are as defined above; and (b) removing the 2'-acetyl group.

13. The process according to claim 12, wherein the hypophosphite reagent is a compound having a formula $M(H_2PO_2)_x$, wherein M is $Na^+$, $NH_4^+$, $K^+$ or $Ca^{++}$, and x is 1 or 2.

14. The process according to claim 12, wherein the phase transfer agent is selected from the group consisting of tetra-n-butylammonium hydroxide, tetraethylammonium hydroxide, benzyl trimethylammonium hydroxide, benzyl triethylammonium hydroxide, tris[2-(2-methoxyethoxy)ethylamine, tetra-n-butylphosphonium bromide, and tetra-n-butylammonium hydrogen sulfate.

15. The process according to claim 13, wherein the phase transfer agent is dissolved in a solution with a water soluble base.

16. The process according to claim 14, wherein the base is triethylamine, diisopropylamine, tetramethylguanidine, N-ethylpiperidine, N-methylpiperidine, and pyrrolidine, tetra-n-butylammonium hydroxide, or a mixture thereof.

17. The process according to claim 12, wherein the free radical initiator is selected from the group consisting of 4,4'-azobis-(4-cyanovaleric acid) (ACVA), 2,2'-azobis[2-(imidazolin-2-yl)propane]dihydrochloride (AIBP), 2,2-azobis(amidinopropane)-dihydrochloride (ABAP), azobis (isobutyronitrile) (AIBN), azobis(cyclohexanecarbonitrile) (ACCN), and 2,2'-azobis[2-methyl-N-(2-hydroxyethyl)propionamide) (AMHP).

18. The process according to claim 12, wherein the solvent is selected from the group consisting of methanol, ethanol, iso-propanol, n-propanol, and 2-methoxyethanol, or a mixture thereof.

19. The process according to claim 12, wherein R is H.

20. The process according to claim 12, wherein R is OH.

21. The process according to claim 12, wherein the process is carried out at a temperature from about 75° C. to about 110° C. for a period of from about 1 to about 24 hours.

* * * * *